(12) United States Patent
Sadahiro

(10) Patent No.: US 9,146,185 B2
(45) Date of Patent: *Sep. 29, 2015

(54) HARDNESS TESTER AND HARDNESS TEST METHOD

(75) Inventor: Shinichi Sadahiro, Otaru (JP)

(73) Assignee: MITUTOYO CORPORATION, Kanagawa (JP)

(*) Notice: Subject to any disclaimer, the term of this patent is extended or adjusted under 35 U.S.C. 154(b) by 551 days.

This patent is subject to a terminal disclaimer.

(21) Appl. No.: 13/471,745

(22) Filed: May 15, 2012

(65) Prior Publication Data

US 2013/0068001 A1    Mar. 21, 2013

(30) Foreign Application Priority Data

Sep. 15, 2011 (JP) .................................. 2011-201305

(51) Int. Cl.
*G01N 3/42* (2006.01)

(52) U.S. Cl.
CPC .......... *G01N 3/42* (2013.01); *G01N 2203/0082* (2013.01); *G01N 2203/0206* (2013.01); *G01N 2203/0647* (2013.01)

(58) Field of Classification Search
CPC ............ G01N 3/42; G01N 2203/0286; G01N 2203/0082; G01N 2203/0078; G01N 2203/0647; G01N 3/40; G01N 2203/0076; G01N 2203/008; G01N 2203/0206; G01Q 60/366; G01Q 30/02
USPC ...................................................... 73/81, 82
See application file for complete search history.

(56) References Cited

U.S. PATENT DOCUMENTS

| 5,146,779 | A   | * | 9/1992 | Sugimoto et al. ................. 73/81 |
| 6,996,264 | B2  | * | 2/2006 | Hauck et al. ................... 382/141 |
| 7,554,655 | B2  | * | 6/2009 | Fairley et al. ............... 356/237.4 |
| 2011/0007033 | A1 | * | 1/2011 | Choi ............................ 345/175 |

FOREIGN PATENT DOCUMENTS

| CN | 101839832 | 9/2010 |
| JP | 7-218410  | 8/1995 |

(Continued)

OTHER PUBLICATIONS

China Office action, dated Apr. 30, 2014 along with an english translation thereof.

*Primary Examiner* — Hezron E Williams
*Assistant Examiner* — Marrit Eyassu
(74) *Attorney, Agent, or Firm* — Greenblum & Bernstein, P.L.C.

(57) ABSTRACT

A hardness tester includes:
an image capture control portion for obtaining an image data of the surface of the sample by controlling and making an image capture portion capture an image of the surface;
an impression region extracting portion that binarizes the image data, applies reduction/expansion processing to the binarized image data, applies a distance conversion processing to the reduction/expansion processed image data, and extracts a closed region corresponding to a contour of the indenter by using the distance-converted image data;
an impression vertex extracting portion that estimates the vertex for measuring the impression based on a profile of the closed region and extracts a point in the binarized image data, as the vertex for measuring the impression, that agrees with a predetermined condition; and
a hardness calculating portion for calculating hardness of the sample based on the vertexes for measuring the impression.

5 Claims, 8 Drawing Sheets

(56) References Cited

FOREIGN PATENT DOCUMENTS

| JP | 07218410 A * | 8/1995 | ............... G01N 3/42 |
| JP | 8-285755 | 11/1996 | |
| JP | 9-61328 | 3/1997 | |
| JP | 9-210893 | 8/1997 | |
| JP | 9-243539 | 9/1997 | |
| JP | 3071956 | 5/2000 | |
| JP | 2003-166923 | 6/2003 | |
| JP | 2004-037424 | 2/2004 | |
| JP | 2004-286541 | 10/2004 | |

* cited by examiner

HARDNESS TESTER AND HARDNESS TEST METHOD

CROSS-REFERENCE TO RELATED APPLICATION

The present U.S. application claims a priority under the Paris Convention of Japanese Patent Application No. 2011-201305 filed on Sep. 15, 2011, which shall be a basis of correction of an incorrect translation.

BACKGROUND

1. Field of the Invention

The present invention relates to a hardness tester and a hardness test method.

2. Description of Related Art

An indentation hardness test method is widely known in which an indenter, whose projected shape onto a plane is a polygon, is indented on a surface of a material to be tested and its hardness is calculated from a diagonal length of the polygon impression formed on the material. Such a test method is frequently used for evaluation of mechanical characteristics of metal materials.

As is generally known, the Vickers hardness test method uses an indenter of regular quadrangular pyramid shape made of diamond. A hardness of a material sample is calculated using a relation between an average length of two diagonal lengths of an impression of the regular quadrangular pyramid formed on a surface of the sample and load for impressing the indenter onto the sample. The Knoop hardness test method uses an indenter of rectangular pyramid shape made of diamond. A hardness of a material sample is calculated using a relation between length of a longer diagonal of an impression of the rectangular pyramid formed on a sample surface and load for impressing the indenter onto the sample.

A hardness tester for such a test method using an image processing technique with a computer is disclosed (JP H7-218410A, for example). The method in Patent Document 1 captures an image of an impression, formed on a surface of a sample by impressing an indenter thereon, using an imaging means such as a CCD camera connected to a computer, extracts a boundary (dot series data) indicating each side of the impression or corner portions of the impression by applying binary processing, etc. to the captured image data, and calculates hardness from values of coordinates of the extracted boundary or corner portion.

A technique is also disclosed in which an initial image data of a surface of a sample is captured before forming an impression by a CCD camera, an impression image data of the surface is captured after forming an impression by the CCD camera, a differential image data between the initial image data and the impression image data is calculated, a diagonal length is calculated by determining coordinates' values of corner portions of the impression and sample hardness is calculated based on the diagonal length and impress load (JP H9-210893A, for example).

JP Patent No. 3071956 discloses following procedure to determine Vickers hardness. An impression formed on a surface of a sample is imaged by a TV camera and the impression image is digitalized in multi-value gradation. A binary (two-value) image is made by detecting an optimum threshold value for the multi-value digital image and two-dimensional noise reduction is performed for the binary image. After that rough positions of four sides of the impression in the image are determined and boundary points of the impression are detected from the rough position. Four multidimensional regression curves of the boundary points are determined and intersection points of the four regression curves are estimated as vertexes of the impression. An impression area is calculated by determining lengths of two crossing diagonals of the four vertexes based on the positions in the coordinates. Vickers hardness can be calculated by the impression area and an indentation load of an indenter.

There is a concern that, however, the above conventional technique may produce a result with low reliability because the four sides of the impression are estimated in four approximated multidimensional curves and the intersection points of the curves are estimated as vertexes of the impression. Therefore, accuracy for determining the vertexes' positions largely depends on quality of the noise reduction. In addition, the conventional technique does not estimate the impression region itself but calculates based on edge (boundary) regions or vertex regions, and thus errors may be included in the results and it may cause less reliable results.

According to the conventional technique above explained, a position and shape of the impression in the image are predicted. Therefore, in the case where there is a scratch parallel to a profile of the impression region, it may cause misrecognition, resulting in an inaccurate test result. In addition, it is assumed in the process of the conventional technique that there is only one impression in the captured image. Therefore, the technique cannot be applied to an image containing a plurality of test samples.

SUMMARY

It is an object of the present invention to provide a hardness tester and a hardness test method that can improve reliability of a test result and can apply to a test including multiple samples.

In accordance with a first aspect of the present invention, provided is a hardness tester for determining hardness of a sample by measuring a size of an impression formed on a surface of the sample, placed on a sample stage, by impressing an indenter with predetermined test load. The hardness tester includes an image capture control means for obtaining an image data of the surface of the sample by controlling an image capture means and making the image capture means capture an image of the surface, an impression region extracting means for extracting an impression region formed on the surface of the sample based on the image data obtained by the image capture control means, an impression vertex extracting means for extracting a vertex for measuring the impression to measure a size of the impression based on the impression region extracted by the impression region extracting means, and a hardness calculating means for calculating hardness of the sample based on the vertexes for measuring the impression extracted by the impression vertex extracting means.

The impression region extracting means binarizes the image data of the surface of the sample, applies a reduction processing and an expansion processing to the binarized image data, applies a distance conversion processing to the reduction/expansion processed image data, and extracts a closed region corresponding to a contour of the indenter by using the distance-converted image data.

The impression vertex extracting means estimates the vertex for measuring the impression based on a profile of the closed region extracted by the impression region extracting means, and extracts a point in the binarized image data, as the vertex for measuring the impression, that agrees with a predetermined condition based on the estimated vertex.

Preferably, the indenter has a contour whose planar shape is rectangular. And the impression vertex extracting means modifies the profile of the closed region extracted by the impression region extracting means so that the profile becomes a combination of lines, extracts direction turning points in the modified profile, determines initial positions of four vertexes based on the extracted points, approximates four assigned lines of four profile lines that connect the determined positions, and estimates intersection points of the approximated four lines as the vertexes for measuring the impression.

Preferably, the hardness tester further includes a display control means that can control a display means so as to display the hardness of the sample calculated by the hardness calculating means.

In accordance with a second aspect of the present invention, provided is a hardness test method using a hardness tester for determining hardness of a sample by measuring a size of an impression formed on a surface of the sample, placed on a sample stage, by impressing an indenter with predetermined test load. The method includes a step of controlling an image capture means so as to capture an image of a surface of a sample to obtain an image data of the surface of the sample; a step of extracting an impression region formed on the surface of the sample based on the image data obtained by the image capture controlling step; a step of extracting vertexes for measuring the impression so as to measure a size of the impression based on the impression region extracted by the impression region extracting step; and a step of calculating hardness of the sample based on the vertexes for measuring the impression extracted by the impression vertex extracting step.

The impression region extracting step binarizes the image data of the surface of the sample, applies a reduction processing and an expansion processing to the binarized image data, applies a distance conversion processing to the reduction/expansion processed image data, and extracts a closed region corresponding to a contour of the indenter by using the distance converted image data.

The impression vertex extracting step estimates the vertexes for measuring the impression based on a profile of the closed region extracted by the impression region extracting step, and extracts points in the binarized image data, as the vertexes for measuring the impression, that agree with a predetermined condition based on the estimated vertex.

According to the present invention, when extracting vertexes for measuring the impression, binarized image data especially before reduction and expansion processing for noise reduction are used. Therefore, more reliable results can be obtained because the vertexes can be extracted without depending on an accuracy of the noise reduction. Because the whole impression region can be estimated instead of selecting a part of the impression region such as an edge portion, vertex portion, or the like, an error contained in a test result can be decreased and thus reliability can be increased. Because a closed region according to a shape of the indenter can be extracted and thus the region can be extracted without depending on a figure of the impression region in the image, a recognition error can be prevented and an accurate test can be performed even when there is a scratch, on a surface of a sample, parallel to a side line of the impression region. In addition, because a plurality of closed regions can be extracted from one image data, the method can be applied to a test including a plurality of samples.

BRIEF DESCRIPTION OF THE DRAWINGS

The present invention will become more fully understood from the detailed description given hereinbelow and the accompanying drawings which are given by way of illustration only, and thus are not intended as a definition of the limits of the present invention, and wherein.

DETAILED DESCRIPTION OF THE PREFERRED EMBODIMENTS

Figure 1:
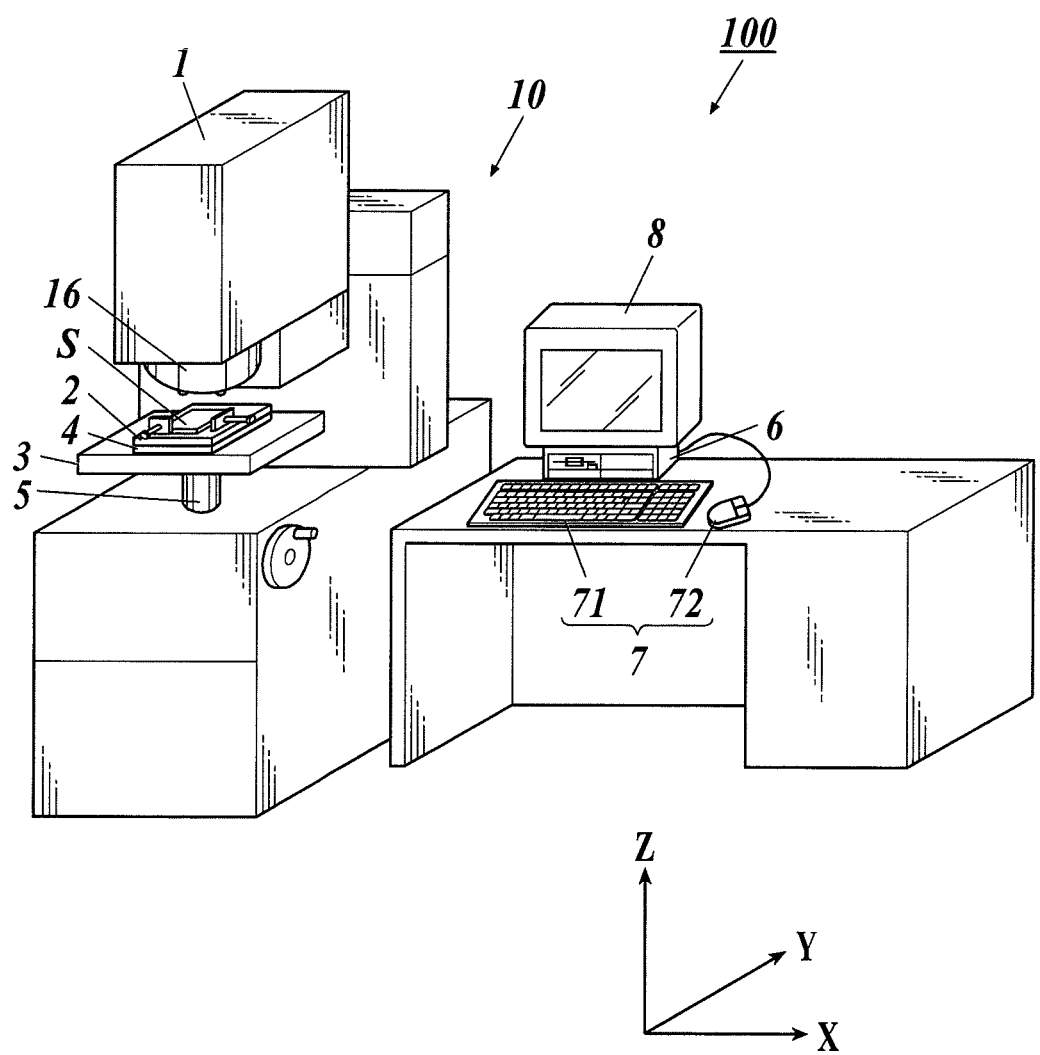
FIG. 1 is a perspective view showing a whole structure of a hardness tester according to an exemplary embodiment of the present invention.

An exemplary embodiment of the present invention will be explained with reference to attached drawings. In the following explanation, the X-axis in FIG. 1 is assumed as right and left directions, the Y-axis is assumed as front and rear and the Z-axis is assumed as up and down. And X-Y plane is assumed as a horizontal plane.

Figure 2:
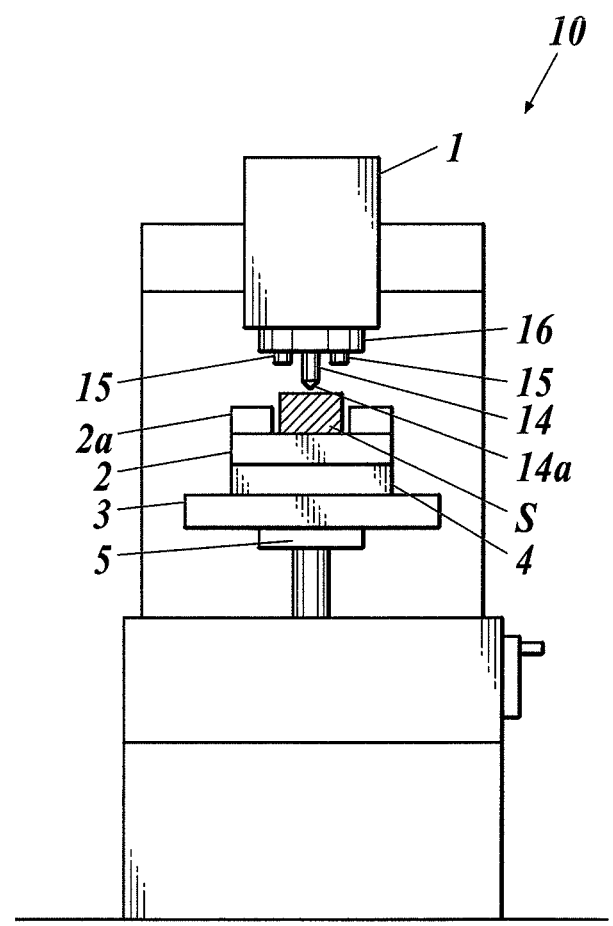
FIG. 2 illustrates a main body of a hardness tester according to an exemplary embodiment.

A hardness tester 100 is a Vickers hardness tester an indenter 14a of which is formed in rectangular as a planar shape, for example. It is provided with a main body 10 of the tester, control portion 6, operating portion 7, monitor 8, etc. as shown in FIGS. 1 and 2.

The main body 10 of the tester is provided with a hardness measurement portion 1 to measure hardness of a sample S, a sample stage 2 to place the sample S, an X-Y stage 3 to shift the sample stage 2, an AF stage 4 to focus on a surface of the sample S, a lifting mechanism 5 to lift or lower the sample stage 2 (and the X-Y stage 3 and AF stage 4), and the like.

Figure 3:
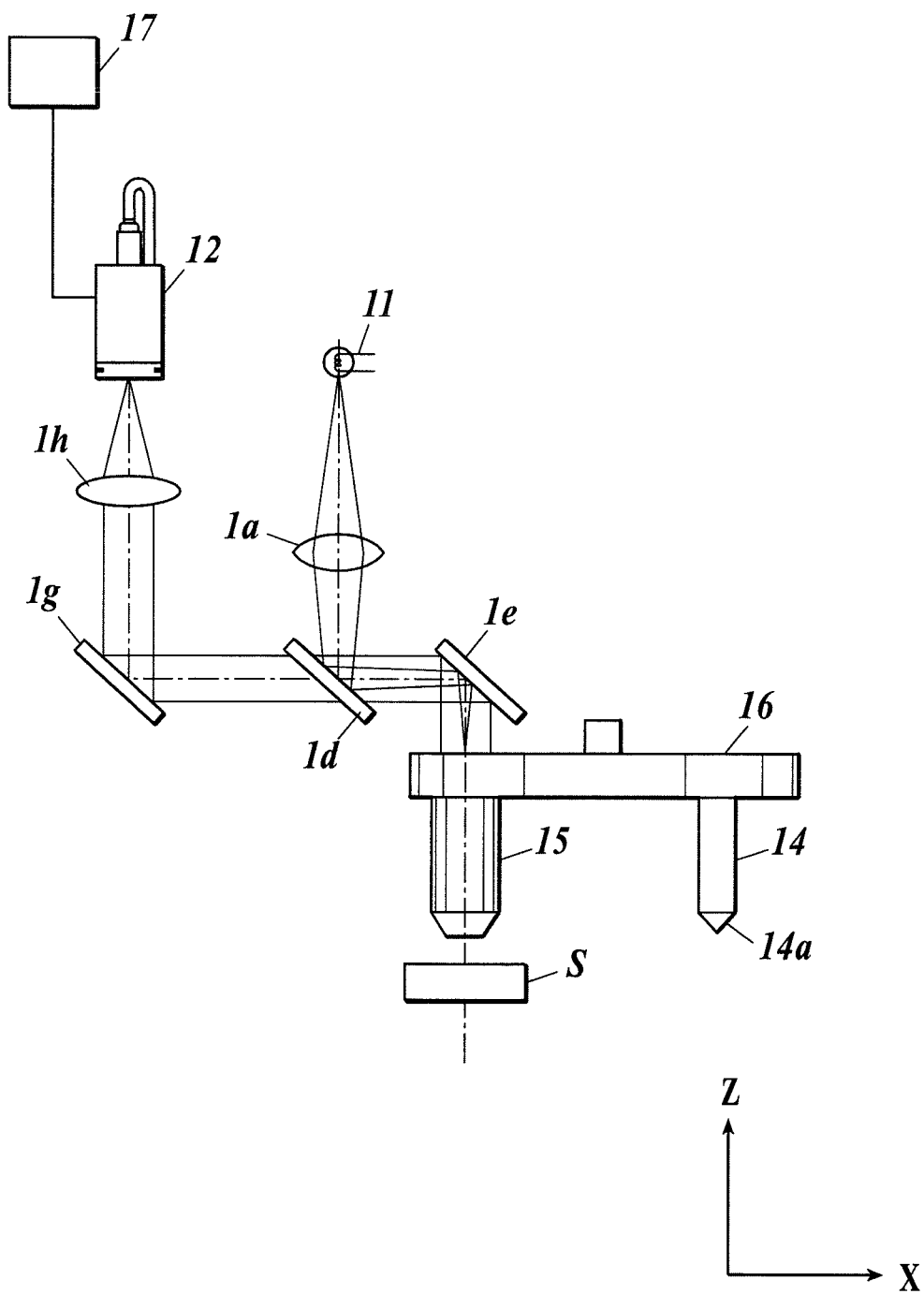
FIG. 3 illustrates a hardness measurement portion of a hardness tester according to an exemplary embodiment.

The hardness measurement portion 1 is composed of, as shown in FIG. 3, for example, a lighting device 11 that illuminates the surface of the sample S, a CCD camera 12 that captures an image of the surface of the sample S and a turret 16 that is provided with an indenter shaft 14 for holding the indenter 14a and an objective lens 15 and can exchange the indenter shaft 14 and the objective lens 15 by rotating itself.

The lighting device 11 illuminates the surface of the sample S by emitting light, and the light emitted from the lighting device 11 passes through a lens 1a, half mirror 1d, mirror 1e and the objective lens 15 to reach the surface of the sample S.

The CCD camera 12 receives reflected light that is emitted from the surface of the sample S and passes through the objective lens 15, mirror 1e, half mirror 1d, a mirror 1g and a lens 1h. The CCD camera 12 thus captures the surface of the sample S and an impression indented by the indenter 14a on the surface of the sample S, obtains an image data and outputs the image data to the control portion 6 through a frame grabber 17 that can store a plurality of frame image data.

The CCD camera 12 functions as an image capture means by the above procedure.

The indenter shaft 14 is advanced toward the sample S placed on the sample stage 2 by a loading mechanism (not shown), which is driven in accordance with a control signal output from the control portion 6, and press the indenter 14a provided at the tip of the shaft onto the surface of the sample S with a predetermined test load.

The objective lenses 15 are collective lenses each having a different magnitude and are held on an underside of the turret 16. The light emitted from the lighting device 11 is impinged uniformly onto the surface of the sample S by rotating the turret 16 and locating the objective lens just above the sample S.

The turret 16 is provided with the indenter shaft 14 and a plurality of objective lenses 15 on the underside thereof and is structured such that one of the indenter shaft 14 and a plurality of objective lenses 15 can be positioned above the sample S by rotating the turret 16 around the Z-axis of the turret 16. As a result, when the indenter shaft 14 is positioned above the sample S, it becomes possible to indent the surface of the sample S, and when one of the objective lenses is positioned above the sample S, it becomes possible to observe the impression indented on the surface.

The sample S on the sample stage 2 is held by a sample holding portion 2a.

The X-Y stage 3 is driven by a driving mechanism (not shown) that is activated by a control signal output from the control portion 6 so as to move the sample stage 2 toward the directions (X-axis and Y-axis directions) orthogonal to the advancing direction (Z-axis direction) of the indenter 14a.

The AF stage 4 is driven by a signal output from the control portion 6, lifts or lowers the sample stage 2 minutely and focuses on the surface of the sample S based on the image data captured by the CCD camera 12.

The lifting mechanism 5 is driven by a signal output from the control portion 6, and changes a relative distance between the sample stage 2 and the objective lens 15 by moving the sample stage 2 (and the X-Y stage 3 and AF stage 4) upwardly or downwardly.

The operating portion 7 is composed of a keyboard 71, mouse 72, and the like, and a user can perform inputting for operation of a hardness test. When a predetermined input operation is performed at the operating portion 7, a predetermined operation signal is output to the control portion 6.

Specifically, a user can select conditions to determine a focusing position on the impression by the keyboard 71 or mouse 72, etc. of the operating portion 7.

A user can determine a moving range (a range of the relative distance between the sample stage 2 and the objective lens 15) of the sample stage 2 (and the lifting mechanism 5 and AF stage 4) by the operating portion 7.

A user can also input test conditions of a hardness test using the hardness tester 100 by the operating portion 7. The input values of the test conditions are transmitted to the control portion 6. The test condition values are, for example, material of the sample S, test load (N) loaded on the sample S by the indenter 14a, magnitude of the objective lens.

A user can also select, by the operating portion 7, a manual mode to determine the focusing position of the impression manually or an automatic mode to perform it automatically.

The monitor 8 is composed of a display device such as a LCD, for example. The monitor displays conditions of a hardness test input from the control portion 7, results of the hardness test, an image of a surface of a sample S or an impression formed on the surface that is captured by the CCD camera 12, and the like. The monitor 8 functions as a display means in this way.

Figure 4:
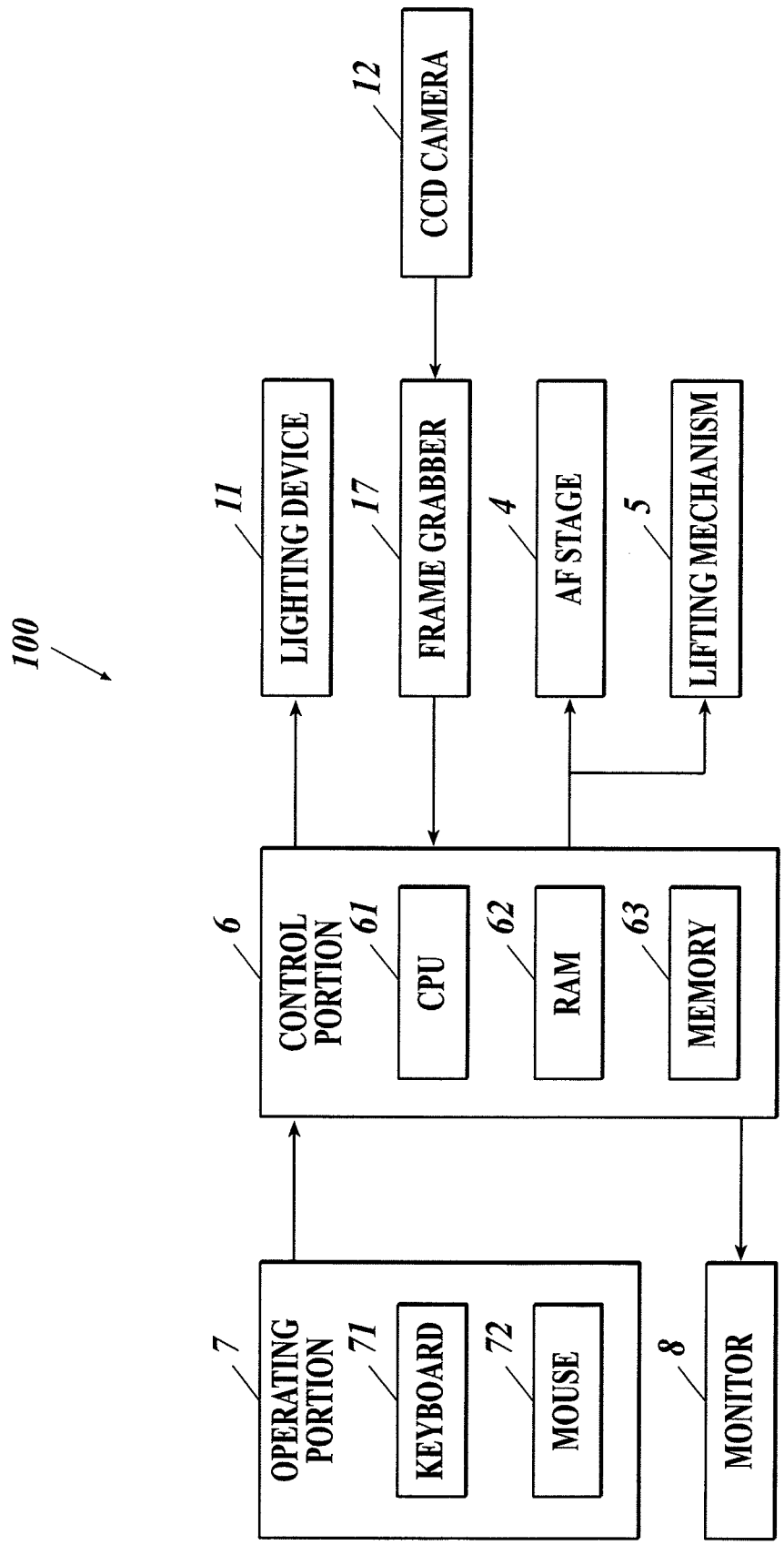
FIG. 4 is a control block diagram of a hardness tester according to an exemplary embodiment.

As shown in FIG. 4, the control portion 6 is composed of a CPU (Central Processing Unit) 61, RAM (Random Access Memory) 62, memory portion 63, and the like. The control portion has a function to control performing a predetermined hardness test by executing a predetermined program stored in the memory 63.

The CPU 61 controls the whole hardness tester 100 by reading a processing program stored in the memory 63 and developing the program in the RAM 62 to execute it.

The RAM 62 develops the program executed by the CPU 61 in a program storing region in the RAM 62 and stores input data and results obtained by executing the program in a data storing region.

The memory 63 includes a recording medium (not shown) for storing a program and/or data and the recording medium is composed of a semiconductor memory, and the like. The memory 63 stores various data by which the CPU 61 can perform controlling the whole hardness tester 100, various processing programs, processed data after prosecution of the programs, and the like. Specifically, the memory 63 stores an X-Y stage control program, auto-focusing program, impression forming program, image capture control program, impression region extracting program, impression vertex extracting program, hardness calculation program, display control program, and the like.

Next, an operation of the hardness tester 100 according to an exemplary embodiment will be explained.

The CPU 61 shifts, by executing an X-Y stage control program stored in the memory 63, the X-Y stage 3 so that a specified region on the surface of the sample S is located just below the CCD camera 12.

Next, the CPU 61 performs, by executing an auto-focusing program stored in the memory 63, auto-focusing on the surface of the sample S by lifting or lowering the AF stage 4 based on the image data obtained by the CCD camera 12 of the hardness measurement portion 1.

And the CPU 61 presses, by executing an impression forming program stored in the memory 63, the indenter 14a onto the surface of the sample S with a predetermined test load to form an impression.

Next, operations of the hardness tester 100 according to an exemplary embodiment after formation of an impression will be explained with reference to the flowcharts of FIGS. 5 to 7. The operations are performed by the CPU 61 by executing various programs stored in the memory 63.

At first, the CPU 61 controls, by executing an image capture control program stored in the memory 63, the CCD camera 12 so as to capture the surface of the sample S and obtains image data of the surface of the sample S (step S1: image capture control step).

Next, the CPU 61 performs, by executing an impression region extracting program stored in the memory 63, an extraction process to extract an impression region formed on the surface of the sample S based on the image data of the surface of the sample S obtained at the step S1 (step S2: impression region extracting step).

Figure 6:
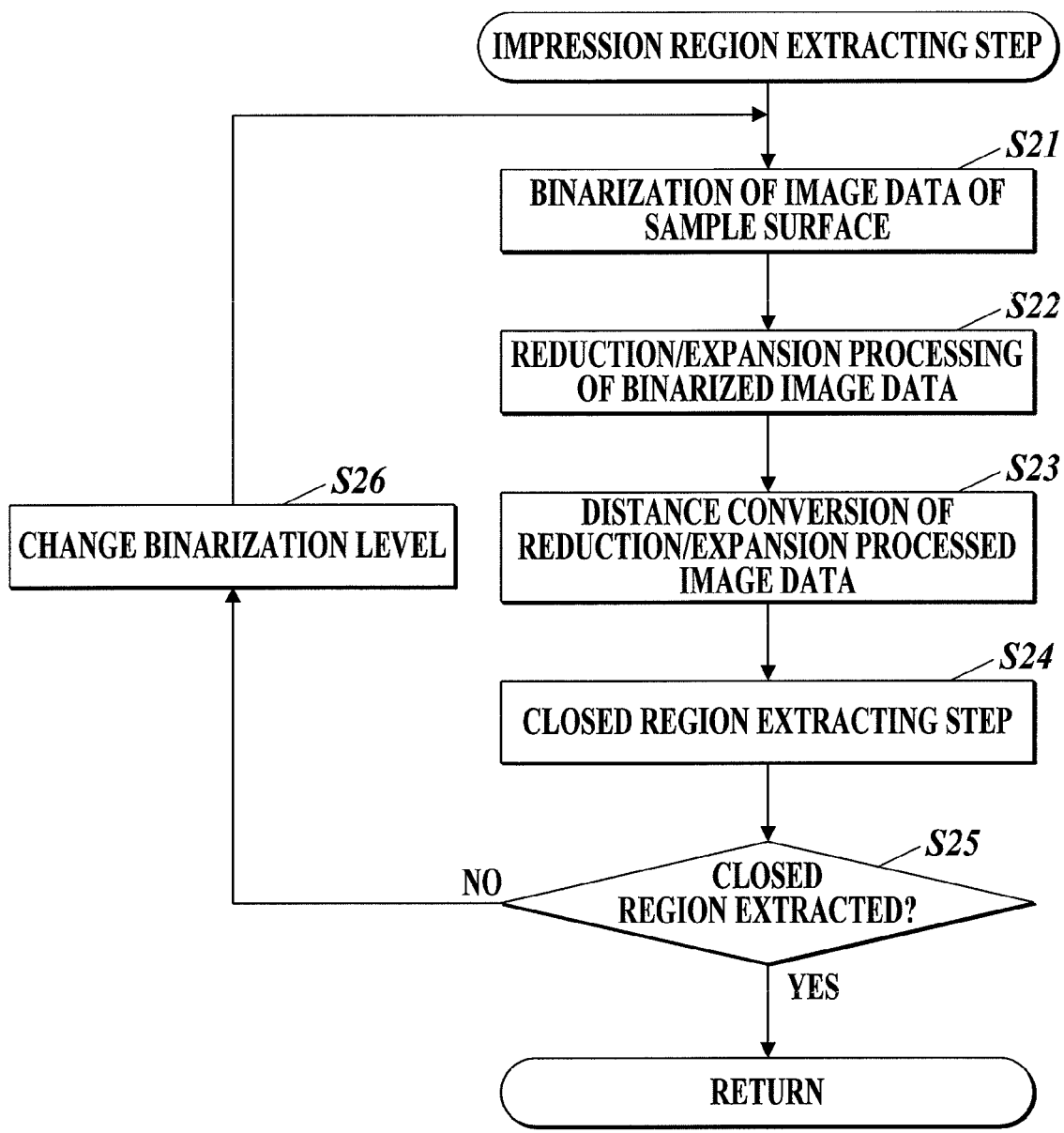
FIG. 6 is a flow chart of impression region extraction steps of a hardness tester according to an exemplary embodiment.

Specifically, as shown in FIG. 6, at first the CPU 61 binarizes the image data of the surface of the sample S obtained at the step S1 (step S21). More specifically, the original gray scale image data (the surface image of the sample S) is converted into two levels of gray. That is, the CPU 61 changes each pixel into white when a brightness of the pixel exceeds a predetermined threshold value and into black when a brightness of the pixel does not reach the threshold value. After the step, a portion changed into black in the surface image data of the sample S becomes darker than the original image and a portion changed into white becomes whiter than the original image. For example, an impression portion formed on the surface of the sample S is less bright than background pixels and thus is converted into black pixels. The binarized image data obtained at the step S21 is stored in the memory 63.

Next, the CPU 61 makes a copy of the binarized image data obtained at the step S21 and performs a reduction processing and an expansion processing to the copied binarized image data (step S22). The "reduction processing" means a processing to reduce (narrow) a black pixel region by one black pixel at a boundary of the black and white pixel regions of the binarized image data. An isolated black pixel and a black projecting pixel can be removed by the processing and thus a noise caused by a damage on the surface of the sample S, and the like can be removed. The "expansion processing" means a processing to extend a black pixel region by one black pixel at the boundary of the black and white pixel regions of the binarized image data. A small trench and a hole of a white pixel can be removed by the processing and thus a profile of the extracted region can be smoothened.

Next, the CPU 61 performs a distance conversion processing to the reduction and expansion processed image data obtained at the step S22 (step S23). The "distance conversion" processing is a processing to assign a distance value to each pixel in the binarized image data such that a shortest distance from the pixel to a white pixel (background pixel) is the distance value of the pixel.

Next, the CPU 61 performs an extracting processing, by utilizing the image data that is distance-converted at the step 23, of a closed region corresponding to a shape of the indenter 14a (step S24). Specifically, the closed region is chain coded by scanning the image data after the distance conversion and a chain code series that can be assumed to be an impression region is stored in the memory 63 based on a result of calculation of an area of the region, predetermined judgment standard value, and the like. The "chain coding" is a technique of coding to represent a direction of a line in eight direction codes (chain codes). The predetermined judgment standard value is a judgment standard obtained by combining compactness of the region calculated by (circumference×circumference)/area, rate of change of chain code calculated by (number of change of the chain code)/(number of the chain code), and the like for judging whether the closed region has a shape of an object to be extracted. Therefore, if an extracted closed region is judged to be too small or have a shape different from the object to be extracted (the shape of the indenter 14a), the closed region is ignored and not stored in the memory 63. Because a closed region can be extracted in accordance with the shape of the indenter 14a as explained in the step S24, the method can be applied to both of Knoop hardness tester and Brinell hardness tester as well as the Vickers hardness tester of an exemplary embodiment.

Next, the CPU 61 judges whether or not a closed region is extracted at the step S24 (step S25). Specifically, the CPU judges whether one or more closed regions are stored in the memory 63. If judged that one or more closed regions are stored in the memory 63, that is, a closed region is extracted (step S25: YES), the impression region extracting step is ceased and the flowchart goes to step S3 shown in FIG. 5. If judged that one or more closed regions are not stored in the memory 63, that is, a closed region is not extracted (step S25: NO), the flowchart goes to step S26.

The CPU 61 changes a level of binarization at the step S26 by changing the threshold value, or the like. The CPU 61 re-performs the impression region extracting step at the step S21 after changing the binarization level.

Figure 5:
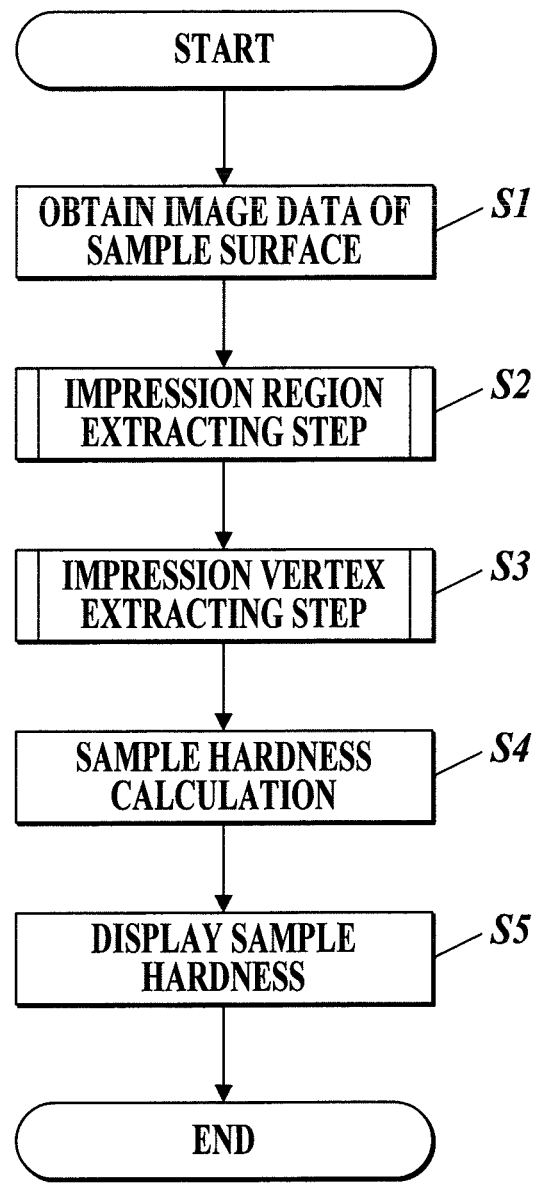
FIG. 5 is a flow chart of performance of a hardness tester according to an exemplary embodiment after indentation.

Next, as shown in FIG. 5, the CPU 61 performs a vertex extracting processing for measuring a size of the impression based on a profile of the closed region extracted in the impression region extracting processing of the step S2 by executing the impression vertex extracting program stored in the memory 63 (step S3: impression vertex extracting step).

Figure 7:
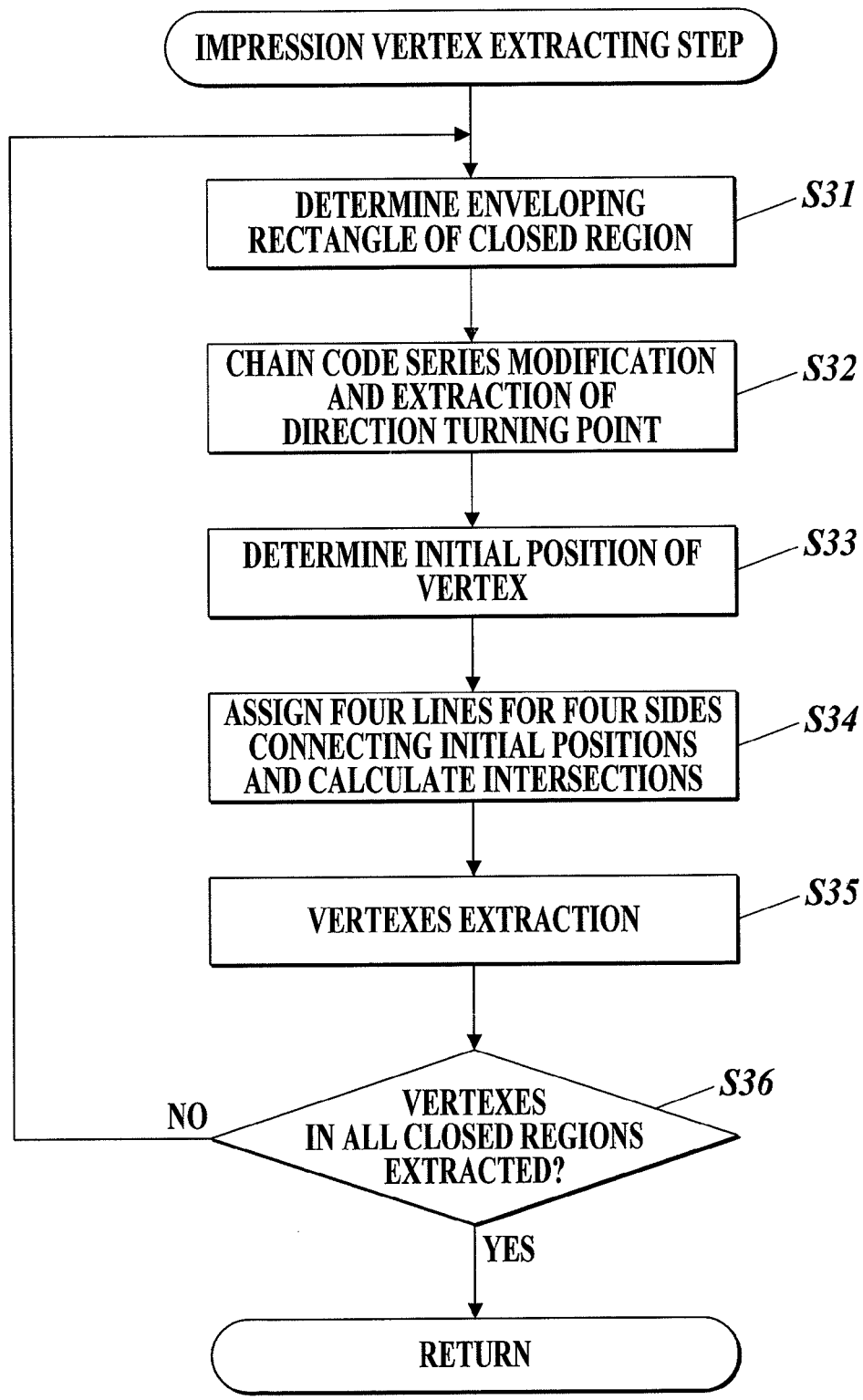
FIG. 7 is a flow chart of impression vertex extraction steps of a hardness tester according to an exemplary embodiment.

Specifically, as shown in FIG. 7, at first the CPU 61 determines a rectangle enveloping the closed region (step S31) based on the chain code series stored in the memory 63 in the step S24 of FIG. 6. More specifically, the enveloping rectangle of the closed region is determined by extracting four points on a closed region boundary whose coordinate values are maximum or minimum. The coordinates are composed of an axis of the image or an inertial main axis and an orthogonal axis thereof.

Next, the CPU 61 modifies the chain code series used in the step S31 and extracts a point that a direction of the series turns (step S32). Specifically, the CPU modifies the chain code series such that the chain code series used in the step S31 becomes a combination of straight lines and extracts points at which the direction of the modified code series turns. The point is a choice of the vertex for measuring the impression.

Next, the CPU 61 determines initial positions of vertexes for measuring the impression (step S33). Specifically, the closest point to each of the four corner points of the enveloping rectangle determined in the step S31 is selected among the direction turning points extracted in the step S32. The selected points are determined as initial positions of the vertexes.

Figure 8:
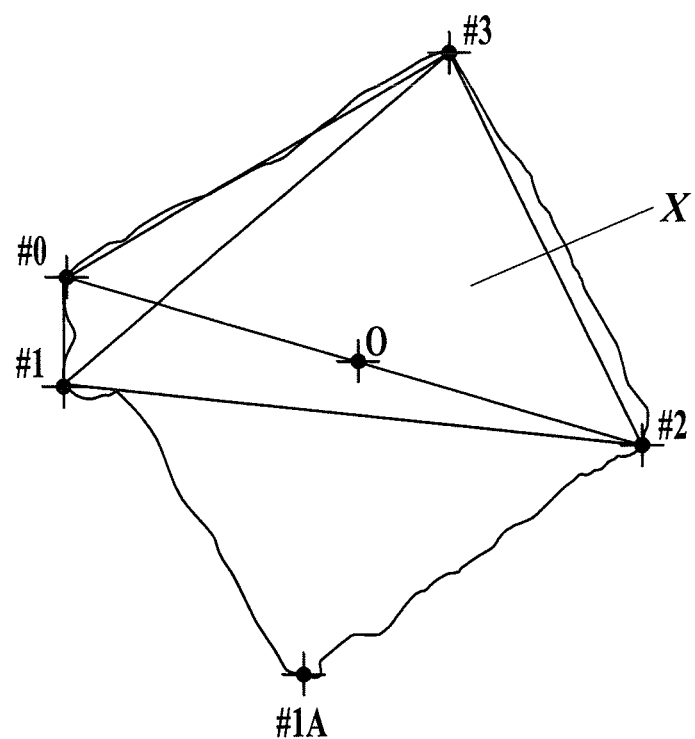
FIG. 8 shows an example how to correct an initial position of a vertex.

Let us assume that the initial positions of the vertexes are determined by point #0, #1, #2 and #3, as shown in FIG. 8, for example. In this case, there is a doubt that the point #1 is improper as an initial position because of the reason that a number of the chain code between the point #0 and point #1 is extremely small (the distance between the points is short) and that a diagonal line connecting the points #1 and #3 is apart from the center O of the closed region X. In such a case, the initial position "point #1" may be changed to "point #1A" that is most apart from the diagonal point #3 among points existing between the point #0 to point #2. As explained above, if the numbers of the chain codes between initial positions are extremely different, it suggests that the result includes improper initial position. Such an improper initial position can be changed to the most apart point from a diagonal point so as to obtain a proper initial position.

Next, the CPU 61 obtains four regression lines, which correspond to four sides, connecting initial positions that are determined in the step S33 and calculates intersection points thereof (step S34). Specifically, four lines are applied, using the robust estimation, to the four sides connecting the initial positions of the vertexes and the CPU 61 calculates four intersection points of the lines formed near the initial positions and estimates the four calculated intersection points as the vertexes for measuring the impression.

Next, the CPU 61 extracts vertexes for measuring the impression (step S35) based on the image data binarized in the step S21 in FIG. 6. Specifically, the CPU 61 extracts points in the image data binarized in the step S21 in FIG. 6, which is the image data before the reduction processing and expansion processing in the step S22 in FIG. 6, that agree with predetermined conditions based on the vertexes extracted in the step S33 as the vertexes for measuring the impression. The point in the binarized image data that agrees with the predetermined conditions is a point satisfying following conditions that it exists near the intersection point that are calculated in the step S34 and it is a point among a dot series on the profile of the closed region. A method to determine a point among a dot series on the profile of the closed region is, for example, to select the nearest point from the intersection point or to select a point where a direction of the dot series turns.

The reason why the image data before the reduction and expansion processing is used, instead of the image data after the processing, is that it may become difficult to extract the vertexes exactly because a corner portion in the profile of the closed region to be a vertex is rounded by the processing. In this embodiment, since the image data before the processing is used, the vertexes of the impression can be extracted exactly.

Next, the CPU 61 judges whether the vertexes for measuring the impression are extracted in all of the closed regions extracted by the step S24 in FIG. 6 (step S36). When judged as the vertexes in all of the closed regions are extracted (step S36: YES), the impression vertexes extracting step is ceased and the flow chart goes to step S4 in FIG. 5. On the other hand, when judged as the vertexes in all of the closed regions are not extracted (step S36: NO), goes to the step S31 and the CPU 61 determines an enveloping rectangle of a closed region in which vertexes are not extracted and performs the impression vertexes extracting step again.

Next, as shown in FIG. 5, the CPU 61 calculates hardness of the sample S, by performing the hardness calculation program stored in the memory 63, based on the vertexes for measuring the impression extracted by the step S3 (step S4: hardness calculation step). Specifically, the CPU 61 calculates lengths of the diagonal lines by referring the coordinate positions of the vertexes for measuring the impression extracted by the step S3 and calculates the hardness of the sample S based on the lengths of the diagonal lines.

Next, the CPU 61 controls the monitor 8 and makes the monitor display the hardness of the sample S calculated by the step S4 by performing the display control program stored in the memory 63 (step S5: display control step).

As explained above, the hardness tester 100 of an exemplary embodiment includes the image capture control means (CPU 61) that controls the CCD camera 12 so as to capture a surface of a sample S and obtain image data of the surface of the sample S, an impression region extracting means (CPU 61) that extracts an impression region formed on the surface of the sample S based on the image data of the surface of the sample S obtained by the image capture control means, an impression vertex extracting means (CPU 61) that extracts vertexes for measuring the impression for measuring a size of the impression based on the impression region extracted by the impression region extracting means, and a hardness calculation means (CPU 61) that calculates hardness of the sample S based on the vertexes for measuring the impression extracted by the impression vertex extracting means. The impression region extracting means binarizes the image data of the surface of the sample S, applies reduction processing and expansion processing to the binarized image data, applies a distance conversion processing to the reduction/expansion processed image data, and extracts a closed region corresponding to a contour of the indenter 14*a* by using the distance converted image data. The impression vertex extracting means estimates the vertexes for measuring the impression based on a profile of the closed region extracted by the impression region extracting means, and extracts points in the binarized image data, as the vertexes for measuring the impression, that agree with a predetermined condition based on the estimated vertexes.

By virtue of these steps, more reliable result can be obtained because, when extracting vertexes for measuring impression, the binarized image data before the reduction and expansion processing for noise removal are used and thus the vertexes can be extracted without influence of reliability of the noise removal. Because the whole impression region, instead of local portions such as edge portions or vertex portions of the impression region, can be estimated, errors contained in a test result can be decreased. It also contributes to reliable estimation. Because the impression region can be extracted without dependence on a direction of the region in the image data by extracting the closed region corresponding to the shape of the indenter 14*a*, it becomes possible to prevent misrecognition even if there is a scratch that is parallel to the impression region on the surface of the sample S and perform a correct test. In addition, because a plurality of closed regions can be extracted from an image data, the method can be applied to a multiple sample test.

Particularly, according to the hardness tester 100 of an exemplary embodiment, the impression vertex extracting means modifies the profile of the region extracted by the impression region extracting means to become linear, extracts direction turning points on the modified profile, determines initial positions of four vertexes based on the extracted points, assigns four regression lines to the four profile lines that connect the determined initial positions, and estimates points of intersection of the four regression lines as the vertexes for measuring the impression. Therefore, it is possible to obtain reliable and high precision test results.

The present invention was explained above in detail with an exemplary embodiment. However, the present invention is not limited to an exemplary embodiment but can be modified within the gist of the invention.

In an exemplary embodiment above explained, for example, when the judgment of the step S25 is NO in FIG. 6 (impression region extracting step), that is, when judged that a closed region is not extracted in the extraction step S24, it is designed to go to the step S26 to change the binarization level. However, the present invention is not limited to that. It is also possible to change a number of the reduction processing and the expansion processing at the step S26 and then go to step S22 to continue the following steps again, for example. It is also possible to set a limitation to the number of the reduction and/or expansion processing. If a closed region is not extracted within the limited number of trials, the binarization level is changed at the step S26 and the flow chart goes to the step S21.

In an exemplary embodiment above explained, the hardness of the sample S calculated at the step S4 (hardness calculation step) of FIG. 5 is displayed by the monitor 8. However, the invention is not limited to that. It is possible to provide a speaker, for example, for audio output and the calculated hardness of the sample S may be output by voice.

In an exemplary embodiment above explained, the image data binarized at the step S21 in FIG. 6 is stored in the memory 63; however, the invention is not limited to that. It is possible to store the data in the RAM 62, for example.

In an exemplary embodiment above explained, a Vickers hardness tester having the indenter 14*a* whose planar shape is a rectangle is assumed as the hardness tester 100; however, the invention is not limited to that. It is possible to apply to a Knoop hardness tester having an indenter whose planar shape is a rectangle or a Brinell hardness tester having an indenter whose shape is sphere. When applying to the Brinell hardness tester, a shape of an impression formed on a surface of a sample S is circle. Therefore, a circular closed region is extracted at the impression region extracting step and arbitrary four points on an outline (profile) of the closed region is estimated as vertexes for measuring impression at the impression vertex extracting step. And points in binarized image data that agree with predetermined conditions are extracted as vertexes of the impression based on the estimated points. It is possible to obtain the same effect as that of the Vickers hardness tester in this way.

It should be noted that a detailed structure, each element or each operation of the hardness tester 100 of an exemplary embodiment above explained can be modified within the gist of the present invention.

What is claimed is:

1. A hardness tester for determining hardness of a sample by measuring a size of an impression formed on a surface of the sample, placed on a sample stage, by impressing an indenter with predetermined test load, comprising:
    an image capture controller for obtaining an image data of the surface of the sample by controlling an image capturer and making the image capturer capture an image of the surface;
    an impression region extractor for extracting an impression region formed on the surface of the sample based on the image data obtained by the image capture controller;
    an impression vertex extractor for extracting a vertex for measuring the impression to measure a size of the impression based on the impression region extracted by the impression region extractor; and
    a hardness calculator for calculating hardness of the sample based on the vertexes for measuring the impression extracted by the impression vertex extractor; wherein
    the impression region extractor binarizes the image data of the surface of the sample, applies a reduction processing and an expansion processing to the binarized image data, applies a distance conversion processing to the reduction/expansion processed image data, and extracts a closed region corresponding to a contour of the indenter by using the distance-converted image data, and upon unsuccessful extraction of the closed region corresponding to the contour of the indenter, changes a level of binarization and thereafter re-extracts the impression region formed on the surface of the sample, and
    the impression vertex extractor estimates the vertex for measuring the impression based on a profile of the closed region extracted by the impression region extractor, and extracts a point in the binarized image data before the reduction processing and the expansion processing, as the vertex for measuring the impression, that agrees with a predetermined condition based on the estimated vertex.

2. The hardness tester of claim 1, wherein
    the indenter has a contour whose planar shape is rectangular, and
    the impression vertex extractor modifies the profile of the closed region extracted by the impression region extractor so that the profile becomes a combination of lines, extracts direction turning points in the modified profile, determines initial positions of four vertexes based on the extracted points, approximates four assigned lines of four profile lines that connect the determined positions, and estimates intersection points of the approximated four lines as the vertexes for measuring the impression.

3. The hardness tester of claim 2, wherein the impression vertex extractor replaces the estimated vertexes for measuring the impression with points, in a dot line on a profile of the closed region in the image data binarized by the impression region extractor, that agree with a predetermined condition.

4. The hardness tester of claim 1, further comprising:
    a display controller that can control a display so as to display the hardness of the sample calculated by the hardness calculating portion.

5. A hardness test method using a hardness tester for determining hardness of a sample by measuring a size of an impression formed on a surface of the sample, placed on a sample stage, by impressing an indenter with predetermined test load, comprising:
    controlling an image capturer so as to capture an image of a surface of a sample to obtain an image data of the surface of the sample;
    extracting an impression region formed on the surface of the sample based on the image data obtained by the image capture controlling;
    extracting vertexes for measuring the impression so as to measure a size of the impression based on the impression region extracted by the impression region extracting; and
    calculating hardness of the sample based on the vertexes for measuring the impression extracted by the impression vertex extracting, wherein
    the impression region extracting binarizes the image data of the surface of the sample, applies a reduction processing and an expansion processing to the binarized image data, applies a distance conversion processing to the reduction/expansion processed image data, and extracts a closed region corresponding to a contour of the indenter by using the distance converted image data, and upon unsuccessful extraction of the closed region corresponding to the contour of the indenter, changes a level of binarization whereafter the extracting the impression region is re-performed, and
    the impression vertex extracting estimates the vertexes for measuring the impression based on a profile of the closed region extracted by the impression region extracting, and extracts points in the binarized image data before the reduction processing and the expansion processing, as the vertexes for measuring the impression, that agree with a predetermined condition based on the estimated vertex.

* * * * *